United States Patent [19]

Yamaguchi et al.

[11] Patent Number: 5,502,393
[45] Date of Patent: Mar. 26, 1996

[54] DENSITOMETER USING A MICROWAVE

[75] Inventors: Seiji Yamaguchi, Sagamihara; Takeshi Yamaura, Narashino; Takatsugu Ogata, Sayama; Tsutomu Suzuki; Ikuo Arai, both of Tokyo, all of Japan

[73] Assignees: Kabushiki Kaisha Toshiba, Kawasaki; Tokyo Metropolitan, Tokyo, both of Japan

[21] Appl. No.: 220,056

[22] Filed: Mar. 30, 1994

[30] Foreign Application Priority Data

Mar. 30, 1993 [JP] Japan ..................... 5-071664

[51] Int. Cl.$^6$ .......................... G01R 27/32; G01N 22/00
[52] U.S. Cl. ............................ 324/639; 324/637
[58] Field of Search ...................... 324/637, 639, 324/76.52, 76.77, 92

[56] References Cited

U.S. PATENT DOCUMENTS

| | | | |
|---|---|---|---|
| 4,486,714 | 12/1984 | Davis et al. | 324/639 X |
| 4,764,718 | 8/1988 | Revus et al. | 324/637 |
| 4,888,547 | 12/1989 | McGinn et al. | 324/637 |
| 5,369,369 | 11/1994 | Cutmore | 324/637 |
| 5,455,516 | 10/1995 | Jean et al. | 324/639 |

FOREIGN PATENT DOCUMENTS

| | | |
|---|---|---|
| 0268399 | 5/1988 | European Pat. Off. . |
| 0487798 | 6/1992 | European Pat. Off. . |
| 59-19846 | 2/1984 | Japan . |

OTHER PUBLICATIONS

Advances in Instrumentation and Control, vol. 47, Pt. 1, 1992, pp. 617–632, John L. Daniewicz, "Improved On-Line Measurement of Water Content and Other Product Mixture Ratios Using Microwave Spectrum Analysis".

Primary Examiner—Kenneth A. Wieder
Assistant Examiner—Glenn W. Brown
Attorney, Agent, or Firm—Oblon, Spivak, McClelland, Maier & Neustadt

[57] ABSTRACT

A densitometer using a microwave comprises a microwave detection section, a phase detection section, and a density calculation section. The microwave detection section picks up a first microwave receiving signal by transmitting and receiving a microwave of a frequency band of 1.4 -{GHz}- to 1.75 -{GHz}- to/from a reference fluid, and a second microwave receiving signal by transmitting and receiving a microwave of a frequency band of 1.4 -{GHz}- to 1.75 -{GHz}- to/from a measuring fluid. The phase detection section obtains a phase difference between the first microwave receiving signal and the second microwave receiving signal. The density calculation section calculates the density of measuring fluid based on the phase difference obtained by the phase detection section.

19 Claims, 6 Drawing Sheets

DENSITOMETER USING A MICROWAVE

BACKGROUND OF THE INVENTION

1. Field of the Invention

The present invention relates to a densitometer using a microwave, and more particularly to a densitometer using a microwave which can measure density of suspension (suspended matter) or dissolving matter with high accuracy.

2. Description of the Related Art

Figure 1:
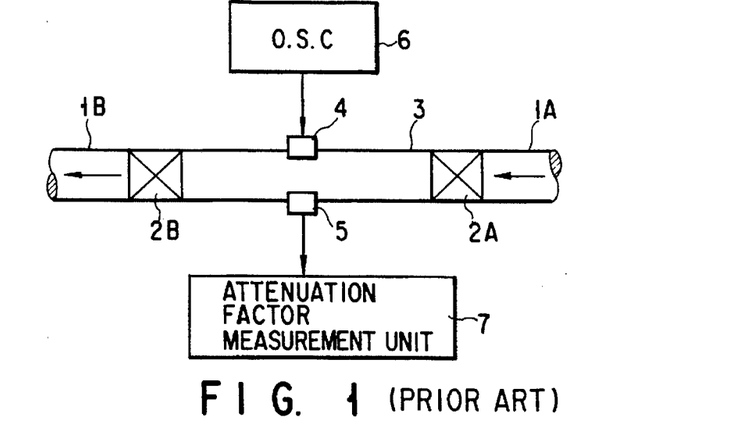
FIG. 1 is a view showing the schematic structure of a conventional densitometer.

As a densitometer for measuring density of suspension (suspended matter) such as sludge and pulp, a densitometer using an ultrasonic wave has been conventionally known. FIG. 1 shows such a conventional densitometer using an ultrasonic wave.

As shown in FIG. 1, a detection pipe 3 is provided between a pipe 1A and a pipe 1B through sluice valves 2A and 2B. On a pipe wall, an ultrasonic transmitter 4 and an ultrasonic receiver 5 are arranged to be opposed to each other so as to contact a measuring fluid flowing in the detection pipe 3. An oscillator 6 is connected to the ultrasonic transmitter 4. An attenuation factor measurement unit 7 is connected to the ultrasonic receiver 5.

According to the above-mentioned densitometer using the ultrasonic wave, the ultrasonic transmitter 4 is driven by the oscillator 6, and an ultrasonic wave is transmitted from the ultrasonic transmitter 4, propagated in fluid of the detection pipe 3, and received by the ultrasonic receiver 5. At this time, strength of the ultrasonic wave is attenuated in accordance with density of the suspension in liquid. The ultrasonic receiver 5 generates an electrical signal in accordance with the receiving strength of the ultrasonic wave. The receiving signal outputted from the ultrasonic receiver 5 is supplied to the attenuation factor measurement unit 7. In the attenuation factor measurement unit 7, there is, in advance, set a working curve showing a relationship between density of suspension and an attenuation factor of the ultrasonic wave in accordance with the density of the suspension. The attenuation factor measurement unit 7 measures density of the suspension within the fluid in accordance with the working curve based on the attenuation factor shown by the receiving signal outputted from the ultrasonic receiver 5.

However, in the above-mentioned densitometer using the ultrasonic wave, the following problems exist.

(a) Since the ultrasonic transmitter 4 and the ultrasonic receiver 5 contact fluid, suspension is adhered to their contact surfaces, and this becomes a factor causing a measuring error. Due to this, it is necessary that the contact surfaces of the ultrasonic transmitter 4 and the ultrasonic receiver 5 be cleaned. Particularly, suspension such as sludge is easily adhered thereto, such that cleaning must be frequently performed.

(b) The above problem can be solved by providing the ultrasonic transmitter 4 and the ultrasonic receiver 5 on the outside of the detection pipe 3. However, in this case, the thickness of a portion of the detection pipe 3 where ultrasonic transmitter 4 and the ultrasonic receiver 5 are located must be thinned in order to decrease the attenuation of the ultrasonic wave in that wall portion of the detection pipe 3. Due to this, there is a problem in strength and durability. Also, the detection pipe 3 is subject to influence of vibration, and this becomes a factor causing a measuring error.

(c) Moreover, as compared with fluid, the attenuation factors of the ultrasonic wave is extremely large in gas. Therefore, if a gas bubble is mixed in the fluid, the attenuation of the ultrasonic wave in gas becomes larger than the attenuation due to suspension. As a result, the density of the measuring fluid cannot be measured. Or, the measuring result having an apparent high density will be obtained.

To solve the above problem, in this type of the densitometer using the ultrasonic wave, there is a densitometer having a bubble erasing mechanism. In the densitometer having a bubble erasing mechanism, a fluid to be measured is introduced into a pressure bubble erasing chamber at a predetermined sampling period. The inside of the pressure bubble erasing chamber is pressurized, and the bubble is dissolved. Thereafter, the density of the suspension within the fluid to be measured is measured by the ultrasonic wave. However, even in this type of the densitometer, since fluid is sampled at the predetermined sampling time, a continuous measurement cannot be performed. Moreover, it is needed that a mechanical movable mechanism be provided since sampling and pressure are performed. Therefore, reliability of the operation is low.

(d) Moreover, the above-mentioned densitometer using the ultrasonic wave uses the fact that the ultrasonic wave is dispersed by the measuring matter and attenuated. Due to this, this type of the densitometer cannot be easily applied to a case that the matter is completely dissolved in fluid.

An object of the present invention is to provide a densitometer using a microwave which can measure density of suspension with high accuracy without causing the disadvantages of a densitometer using an ultrasonic wave.

SUMMARY OF THE INVENTION

The above object can be achieved by the following densitometer.

More specifically, according to the present invention, there is provided a densitometer using a microwave comprising: a microwave detection section for picking up a first microwave receiving signal by transmitting and receiving a microwave of a frequency band of 1.4 -[GHz]- to 1.75 -[GHz]- to/from a reference fluid, and a second microwave receiving signal by transmitting and receiving a microwave of a frequency band of 1.4 -[GHz]- to 1.75 -[GHz]- to/from a measuring fluid; a phase detection section for obtaining a phase difference between the first micro-wave receiving signal and the second microwave receiving signal; and a density calculation section for calculating the density of the measuring fluid based on the phase difference obtained by the phase detection section.

Moreover, the above object can be achieved by the following densitometer.

More specifically, according to the present invention, there is provided a densitometer using a microwave comprising: a microwave detection section for picking up a first microwave receiving signal by transmitting and receiving a microwave of a frequency band of 1.4 -[GHz]- to 1.75 -[GHz]- to/from a reference fluid, and a second microwave receiving signal by transmitting and receiving a microwave of a frequency band of 1.4 -[GHz]- to 1.75 -[GHz]- to/from a measuring fluid; a phase detection section for obtaining a phase difference between the first micro-wave receiving signal and the second microwave receiving signal; a correction section for correcting the phase difference based on a difference between at least one of the first conductivity and first temperature of the reference fluid and at least one of the second conductivity and second temperature of the measuring fluid; and a density calculation section for calculating the density of the measuring fluid based on the corrected phase difference obtained by the correction section.

According to the densitometer using a microwave, the microwave of the frequency band of 1.4 to 1.75 [GHz] is propagated in fluid containing substantially no measuring matter and fluid containing the measuring matter, and phase lags $\theta_A$ and $\theta_B$ are respectively measured. Then, a phase difference $\Delta\theta$ is obtained from these phase lags $\theta_A$ and $\theta_B$. Thereafter, by use of a working curve showing the relationship between a predetermined known density and the phase difference, the density of the fluid is measured.

Also, even in the case that suspension is dissolved in fluid, the microwave is propagated as being influenced by the dissolved matter, and reaches a receiving system. Due to this, the density of the measuring matter can be suitably measured.

Moreover, in the case that the densitometer is applied to the actual pipe to which the fluid to be measured flow, microwave transmission and receiving antennas are closely attached to opening windows opposite to each other through an insulation member for an antenna attachment. Then, the microwave of the frequency band of 1.4 to 1.75 [GHz] is transmitted and received. Due to this, a characteristic of a high transmission factor can be obtained, so that the density of the fluid to be measured can be measured with a high accuracy.

The phase difference is corrected not to be influenced by the conductivity of the measuring fluid and the temperature thereof, so that the density of the measuring fluid can be measured with a high accuracy.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the appended claims.

BRIEF DESCRIPTION OF THE DRAWINGS

The accompanying drawings, which are incorporated in and constitute a part of the specification, illustrate presently preferred embodiments of the invention, and together with the general description given above and the detailed description of the preferred embodiments given below, serve to explain the principles of the invention.

DETAILED DESCRIPTION OF THE PREFERRED EMBODIMENT

A density measuring principle of a densitometer using a microwave of the present invention will be explained with reference to FIGS. 2 and 3.

The densitometer shows the degree of the content of the matter in fluid, that is, the rate of the matter having various components existing in the constant fluid. In other words, the rate can be expressed by the general terms such as content, concentration, or density, etc.

The units of these parameters such as content, concentration, or density etc used in this specification will be explained as follows, and any units can be specified in the present invention.

(1) Percentage by volume, which means a 100× ratio of volume of a compound contained in the matter under the same pressure to volume of the matter, and can be expressed by vol %.

(2) Percentage by weight, which means a 100× ratio of the weight of a compound contained in the matter to the weight of the matter, an can be expressed by wt %.

(3) Molarity, which means concentration of solution containing 1000 g of dissolved molecule in 1 m$^3$ of solution, and can be expressed by mol. Generally, this is used as concentration containing 1 g of dissolved molecule in 1 liter of solution.

(4) Normal, which means concentration of solution containing the equivalent weight of 1000 g of soluble in 1 m$^3$, and can be expressed by N. Generally, this is used as concentration containing the equivalent weight of 1 g of soluble in 1 liter of solution.

In addition to the above, the following display methods.

(5) Number of gram of the matter dissolved in 1 liter of solution. This can be called as g concentration, and expressed by g/l. Also, in this case, solution can be expressed by 100 cm$^3$.

(6) Concentration containing 1 g of soluble in 1000 g of solution. This is also called molarity. In order to distinguish from the case of item (3), this is called as molarity by weight and the case of item (3) is called as molarity by volume.

(7) A ratio of the number of mols of one soluble to solvent in solution and the total number of mols of soluble. This is called as a molar fraction or a molecular rate.

(8) Number of mols of soluble dissolved in 1000 g of solvent. This is called as a molar composition.

In the present invention, the above-mentioned parameters such as content, concentration, or density etc can be also called as density of fluid.

In the densitometer using the microwave of the present invention, a transmission antenna 11 of a microwave and a receiving antenna 12 are provided on the outside of a metallic pipe 10 (hereinafter called as "insulation pipe") comprising an insulation pipe, a case or a partially insulating member to be opposed to each other in a state that these antennas are adhered thereto. A microwave is transmitted from the transmission antenna 11, and received by the receiving antenna 12.

Figure 2:
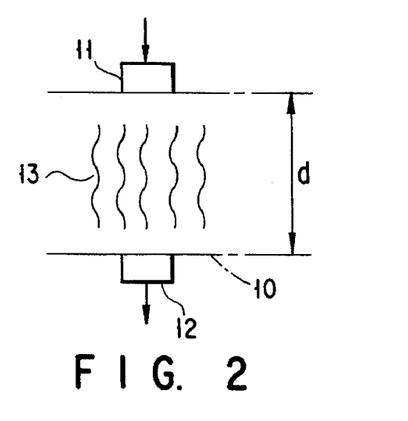
FIGS. 2 and 3 are views explaining a density measuring principle of a densitometer, respectively.

As shown in FIG. 2, in a case that a reference fluid 13 having essentially no impurity such as water is contained in the insulation pipe 10, the microwave is passed through a wall of the insulation pipe 10, propagated in the reference fluid 13, and received by the receiving antenna 12 provided at the opposite side. At this time, a phase lag of a microwave receiving wave is set to $\theta_A$.

Figure 3:
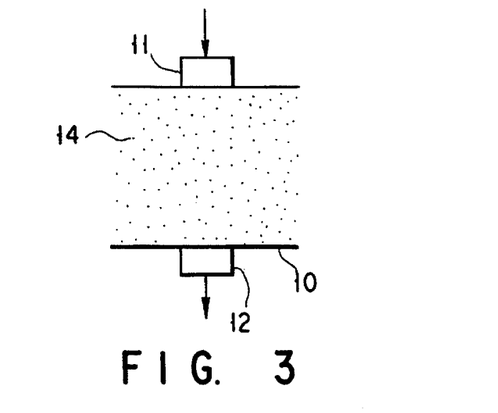

On the other hand, as shown in FIG. 3, in a case that measuring fluid containing suspension is flowed in the insulation pipe 10, the microwave is transmitted from the transmission antenna 11. The microwave is passed through the wall of the insulation pipe 10, propagated in the measuring fluid 14 having the measuring matter, and received by the receiving antenna 12 provided at the opposite side. At this time, a phase lag of a microwave receiving wave is set to $\theta_B$.

These phase lags $\theta_A$ and $\theta_B$ can be obtained from the following equations.

$$\theta_A = \frac{d}{C_0} \left[ \frac{1}{2} \omega \left( \sqrt{\omega^2 \epsilon_W^2 + \frac{\sigma_W^2}{\epsilon_0^2}} + \omega \epsilon_W \right) \right]^{1/2} \quad (1)$$

$$\theta_B = \frac{d}{C_0} \left[ \frac{1}{2} \omega \left( \sqrt{\omega^2 \epsilon_S^2 + \frac{\sigma^2}{\epsilon_0^2}} + \omega \epsilon_S \right) \right]^{1/2} \quad (2)$$

wherein
 $C_0$: a propagation speed of the microwave in a vacuum;
 d: a thickness (distance) of a measuring fluid layer;
 $\omega$: an angular frequency of an incoming microwave
 $\epsilon_0$: a dielectric constant of a vacuum;
 $\epsilon_W$: a relative dielectric constant of a reference fluid;
 $\epsilon_S$: a relative dielectric constant of a measuring fluid to be measured;
 $\sigma_W$: a conductivity of a reference fluid; and
 $\sigma$: a conductivity of a reference fluid.

By use of the above phase lags $\theta_A$ and $\theta_B$, a phase difference $\Delta\theta$ can be obtained from the following equation:

$$\Delta\theta = \theta_A - \theta_B \quad (3)$$

$$\theta_B = \frac{d}{C_0} \left[ \frac{1}{2} \omega \left( \sqrt{\omega^2 \epsilon_S^2 + \frac{\sigma^2}{\epsilon_0^2}} + \omega \epsilon_S \right) \right]^{1/2}$$

$$\theta_A = \frac{d}{C_0} \left[ \frac{1}{2} \omega \left( \sqrt{\omega^2 \epsilon_W^2 + \frac{\sigma_W^2}{\epsilon_0^2}} + \omega \epsilon_W \right) \right]^{1/2}$$

Figure 4:
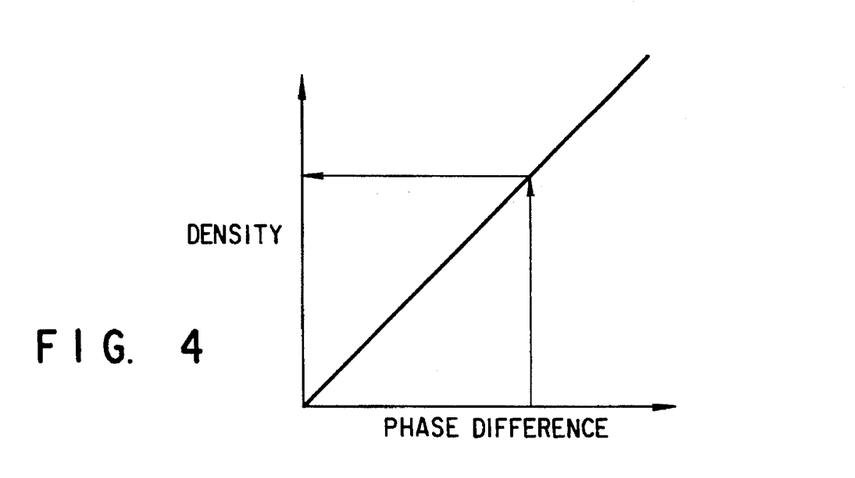
FIG. 4 shows a view showing one example of a working curve.

As is obvious from the above equation, $\Delta\theta$ is a function of $\epsilon_S$, and $\epsilon_S$ is a function of the measuring fluid. Thereby, the phase difference $\Delta\theta$ is regarded as a function of density. Therefore, for measuring the density of the measuring fluid containing the measuring matter such as suspension, the phase lags $\theta_A$ and $\theta_B$ are measured based on the measuring principle shown in FIGS. 2 and 3, and the phase difference $\Delta\theta = \theta_B - \theta_A$ can be obtained from the phase lags $\theta_A$ and $\theta_B$. Thereafter, by use of a working curve showing the relationship between a predetermined known density and the phase difference as shown in FIG. 4, density of the measuring fluid can be measured from the measured phase difference $\Delta\theta$.

A first embodiment of the densitometer using a microwave of the present invention based on the above-mentioned principle of the present invention will be explained with reference to FIGS. 5 to 10.

Figure 5:
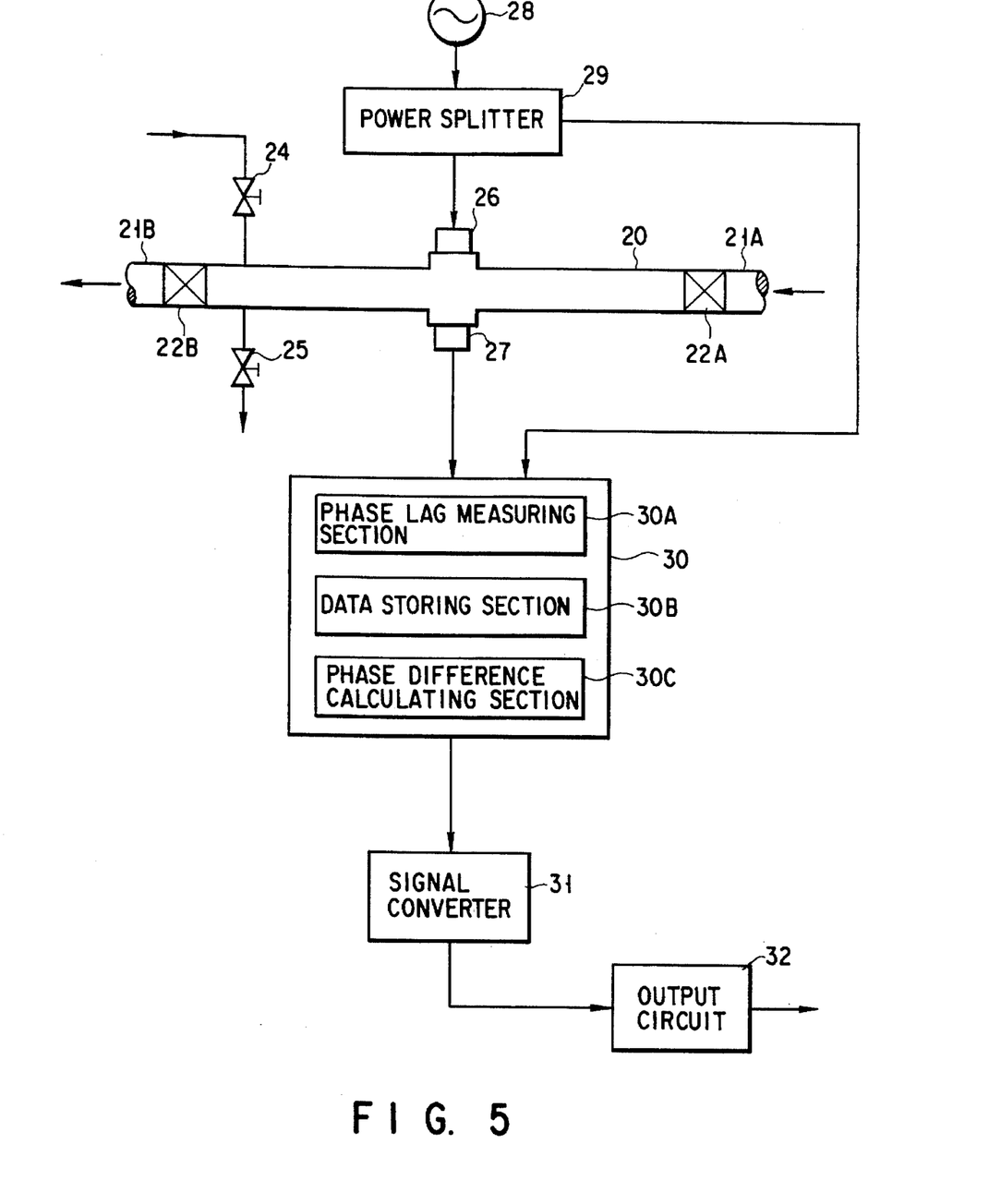
FIG. 5 is a view showing an embodiment of a densitometer using a microwave of the present invention.

In FIG. 5, a density detection pipe 20 is provided between an upper stream side pipe 21A and a lower stream side pipe 21B through sluice valves 22A and 22B. In the density detection pipe 20, a water supply valve 24 and a water exhaust valve 25 are provided so that the reference fluid can be introduced from the external section.

Figure 6:
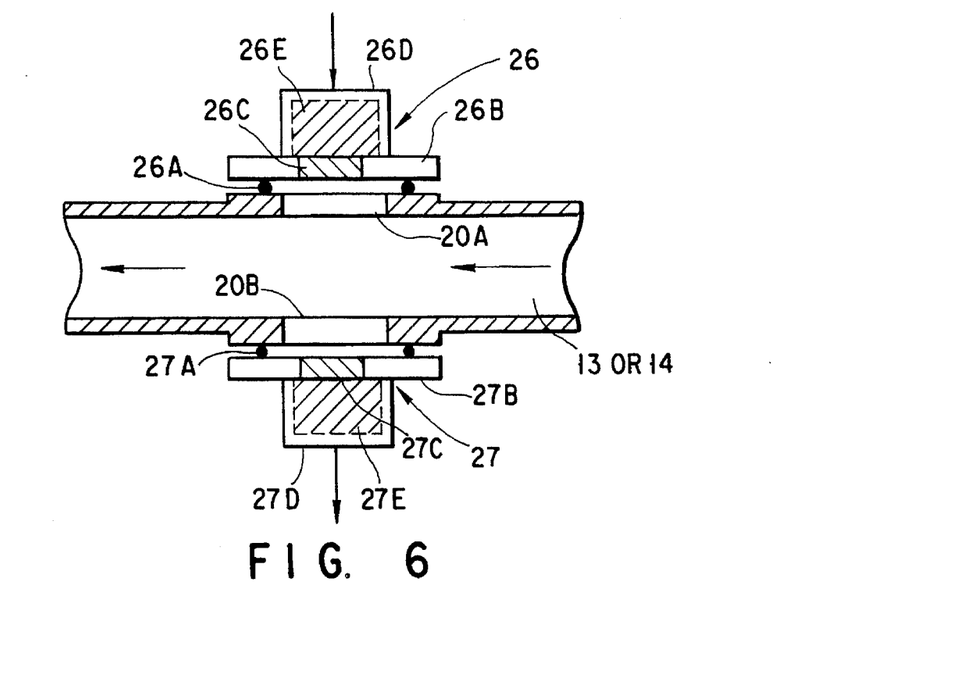
FIG. 6 is a view showing a main part of a portion where an antenna of the densitometer is attached in the embodiment of the present invention.

More specifically, in the density detection pipe 20, as shown in FIG. 6, there are provided opening windows 20A and 20B, which are respectively used for inputting and outputting a microwave, to be opposite to each other. Antenna attaching plates 26B and 27B are attached to the opening windows 20A and 20B through air-tight seal packings 26A and 27A, respectively. In order to keep airtightness of the portions corresponding to the input and output of the microwave, insulation materials 26C and 27C or an entire insulated materials are inserted into the antenna attaching plates 26B and 27B.

A transmission antenna 26D and a receiving antenna 27D are individually closely attached to the antenna attaching plates 26B and 27B. Dielectrics 26E and 27E such as ceramic are packed in the antennas 26D and 27D.

Backing to FIG. 5, the structure of the densitometer using a microwave of the embodiment of the present invention will be explained.

In a transmission system of the densitometer, there is provided a microwave generator 28 for generating the microwave. The output of the microwave generator 28 is sent to the transmission antenna 26 through a power splitter 29.

On the other hand, in a receiving system, a phase detector 30 is provided in the receiving antenna 27. A part of a microwave transmitting wave, serving as a reference signal, is introduced to the phase detector 30 together with the receiving wave of the microwave sent from the receiving antenna 27.

The phase detector 30 comprises a phase lag measuring section 30A for measuring the phase lags $\theta_A$ and $\theta_B$ under the measuring conditions shown in FIGS. 2 and 3, a measuring data storing section 30B for storing these phase lag data, and a phase difference calculating section 30C for obtaining a phase difference $\Delta\theta$. A signal converter 31 receives a signal corresponding to the phase difference from the phase detector 30, converts the signal corresponding to density of, for example, 0 to 5%, i.e., an electrical signal of 4 to 20 [mA].

The following will explain a density measuring operation of the above-structured densitometer of the embodiment of the present invention.

First, as shown in FIG. 5, a reference fluid, for example, water which does not contain impurity suspension, is supplied to the density detection pipe 20, and the phase lag $\theta_A$ is measured. In this case, the phase lag means the phase lag of the microwave receiving wave to the microwave transmission wave, which was obtained by the phase detector 30.

In measuring the phase lag $\theta_A$, after closing the sluice valves 22A and 22B, the water exhaust valve 25 is opened to exhaust measuring fluid such as sludge from a prior measurement from the pipe 20. Thereafter, the water supply valve 24 is opened to supply water and the inside of the pipe 20 is cleaned. Thereafter, the exhaust valve 25 is closed, and the inside of the pipe 20 is filled with water which then serves as a reference fluid.

After the inside of the pipe 20 is filled with the reference fluid, if the microwave signal is generated by the generator 28, the microwave is transmitted from the transmission antenna 26 through the power splitter 29, propagated through the reference fluid in the pipe 20, and received by the receiving antenna 27. The microwave received by the receiving antenna 27 is sent to the phase detector 30. A part of the microwave transmission wave is sent to the phase detector 30 from the power splitter 29.

The phase lag measuring section 30A of the phase detector 30 measures the phase lag $\theta_A$ by comparing the microwave transmission wave with the microwave receiving wave, and the measured phase lag $\theta_A$ is stored in the data storing section 30B.

Thereafter, the exhaust valve 25 is opened to exhaust the reference fluid in the pipe 20. Then, the sluice valves 22A and 22B are opened to allow the measuring fluid including the measuring matter to flow, and the phase lag $\theta_B$ of the measuring fluid is measured. In other words, in a state that the measuring fluid including the measuring matter flows, the microwave is transmitted at a predetermined period or at random. Then, the phase lag $\theta_B$ is measured by the phase detector 30, and the measured phase lag $\theta_B$ is stored in the data storing section 30B. The measured phase lag $\theta_B$ is sequentially renewed as required, and stored therein.

Moreover, in the phase difference calculating section 30C of the the phase detector 30, the phase lag $\theta_B$ and the already-measured phase lag $\theta_A$ at the time of supplying the reference fluid are read from the data storing section 30B, and a phase difference $\Delta\theta$ is obtained based on the following equation to be transmitted to a signal converter 31.

$$\Delta\theta = \theta_B - \theta_A$$

The signal converter 31 receives the phase difference $\Delta\theta$, obtains the relationship between the known density and the phase difference, that is, density, in accordance with the working curve, converts the phase difference to a signal corresponding to the obtained density, and outputs the signal.

The above description explained the principle of the densitometer using the microwave and the structure of the embodiment. The following will explain how degree of the frequency of the microwave is actually used to efficiently and accurately measure the density of the fluid to be measured including the measuring matter. More specifically, an experiment for obtaining a suitable frequency was carried out and the example of the experiment and the experimental result will be explained.

In order to efficiently and accurately measure the density of the measuring fluid containing suspension, we first paid attention to the following point before the experiment.

That is, the attenuation factor of the microwave, which is propagated in the measuring fluid and received, is the smallest. In other word, the use of the frequency of the microwave having a high transmission factor is effective.

Figure 7:
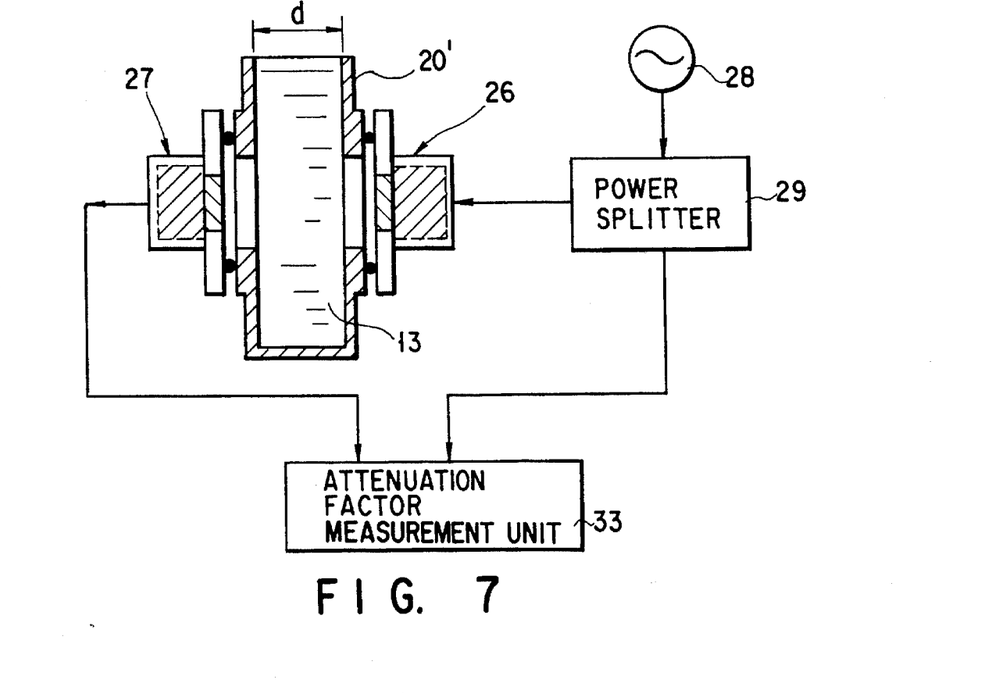
FIG. 7 is a view of an experimental apparatus for measuring an attenuation factor of a microwave and a transmission factor thereof.

Then, in order to obtain the frequency of the microwave having the highest transmission factor, an experiment was carried out by an apparatus shown in FIG. 7. As an apparatus, a case 20' with a bottom plate having substantially the same structure as the detection pipe 20 was used. The inside of the case 20' was filled with water as a reference fluid. Moreover, in the transmission system, similar to FIG. 5, the microwave generator 32, the power splitter 29, and the transmission antenna 26 were provided. In the receiving system, in addition to the receiving antenna 27, an attenuation factor measurement unit 33 was newly used in place of the phase detector 30.

Figure 8:
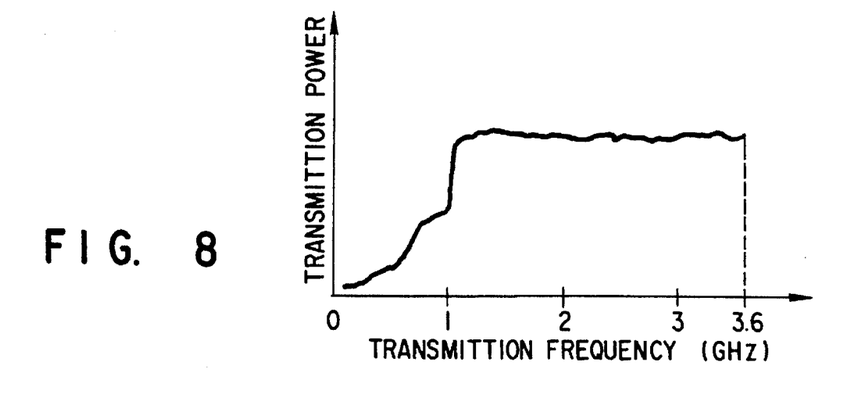
FIGS. 8 to 10 are views showing various frequency characteristics of the microwave obtained by the experimental apparatus shown in FIG. 7.

If a microwave of, e.g., 0 to 3.6 {GHz} is generated from the microwave generator 28 by use of the above experimental apparatus, as shown in FIG. 8, a transmission frequency characteristic in which the microwave is passed through the power splitter 29 and transmitted to water from the transmission antenna can be obtained. In other words, the microwave having substantially the same transmission output characteristic can be incident in the frequency band of 1.0 to 3.6 GHz.

The microwave is propagated in water, and received by the receiving antenna 27. However, a microwave B received by the receiving antenna 27 is sent to the attenuation factor measurement unit 33. At this time, a transmission microwave A is inputted to the attenuation factor measurement unit 33 from the power splitter 29. Therefore, in the attenuation factor measurement unit 33, if the calculation of B/A is carried out by use of the respectively inputted microwaves A and B, a value corresponding to the attenuation factor can be measured.

Figure 9:
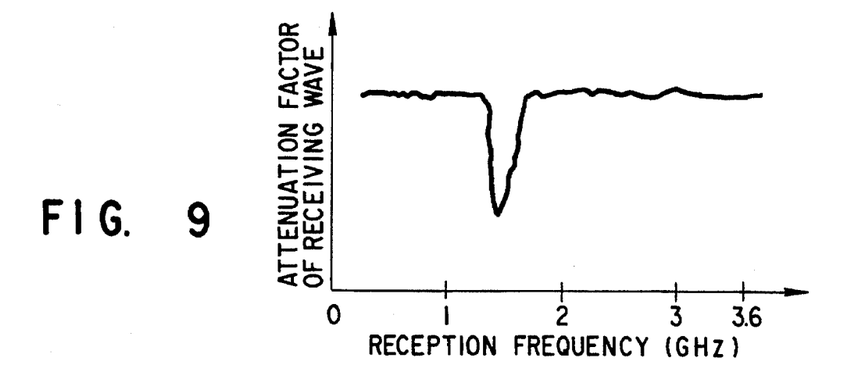
Figure 10:
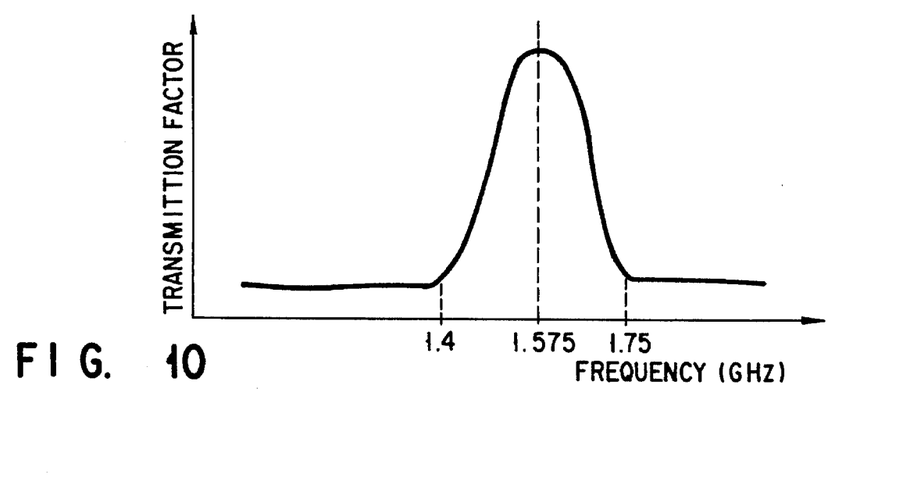

Then, the relationship between the measured result of the attenuation factor measurement unit 33 and the reception frequency was checked. As a result, substantially the constant attenuation factor was obtained as shown in FIG. 9. However, it was found out that the attenuation factor was extremely low at the reception frequency of 1.5 {GHz}. Moreover, the reception frequency band of about 1.5 {GHz} was more precisely reviewed, and the transmission factor (an inverse of the attenuation factor) was measured. As a result, it was found out that the transmission factor of the microwave of the reception frequency band of 1.40 to 1.75 {GHz} whose center is about 1.575 {GHz} was higher than that of the microwave of the other reception frequency bands (FIG. 10).

In addition, various experiments were carried out by use of the case 20' having the various sizes d of 80, 100, 200, 250, 300, 350, and 400 mm (size d corresponds to the diameter of the pipe). As a result, the same result was obtained in any size of the case 20'.

Therefore, as is obvious from the above experiment, it can be understood that the measuring result having the highest accuracy can be obtained if the transmission and receiving are performed by use of the microwave of the frequency band of 1.55 to 1.60 {GHz}. Moreover, it can be understood that the attenuation factor becomes lower than the other frequencies even if the microwave of the reception frequency band of 1.4 to 1.75 {GHz} is used.

The present invention is not limited to the above 10 embodiment. For example, in the above embodiment, the density was measured in the state that sludge flowed. However, the density may be measured in a state that sludge is stationary. Moreover, the present invention can be applied to a case of measuring density of another fluid other than sludge. Furthermore, the above embodiment explained that fluid whose density is 0% was used as a reference. However, it is possible to use fluid whose density is substantially zero. Also, the measuring matter having a known density may be used as a reference. Moreover, an electrical circuit having a constant propagation characteristic may be used as a reference. Furthermore, density may be measured by use of a case or a by-pass pipe in place of the detection pipe 20 and the structure shown in FIG. 5 or 6.

A second embodiment of the present invention using a densitometer using a microwave will be explained with reference to FIGS. 11 to 14.

Figure 11:
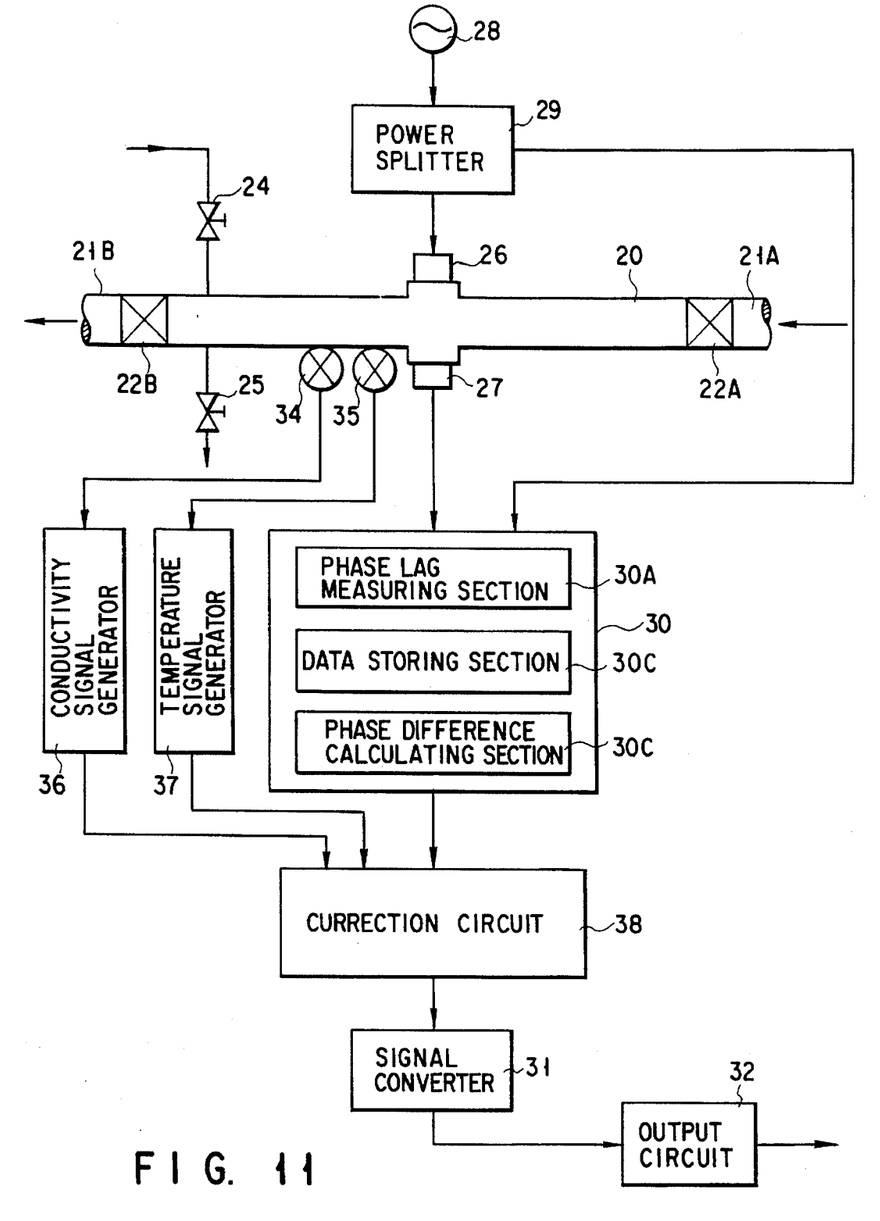
FIG. 11 is a view showing the other embodiment of the densitometer using a microwave of the present invention.

In the second embodiment, a conductivity measuring device 34 and a temperature measuring device 35 are provided in the detection pipe 20. An output of the conductivity measuring device 34 is inputted to a conductivity signal generator 36, and a conductivity signal corresponding to the conductivity is generated. An output of the temperature measuring device 35 is inputted to a temperature signal generator 37, and a temperature signal corresponding to the temperature is generated. The conductivity signal and the temperature signal are supplied to a correction circuit 38. An output of the phase detector 30 other than the conductivity signal and the temperature signal is also inputted to the correction circuit 38.

In the correction circuit 38, the output correction of the phase detector 30 can be selectively performed by the conductivity correction and the temperature correction. Also, the output correction of the phase detector 30 can be performed by the conductivity correction and the temperature correction.

The conductivity correction will be explained with reference to FIG. 12.

Figure 12:
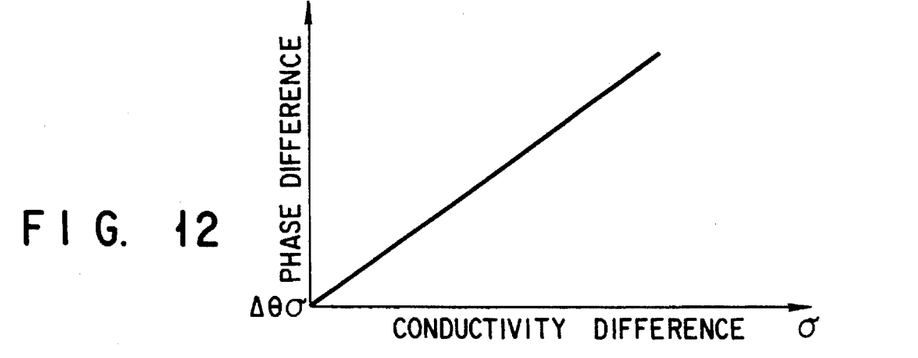
FIGS. 12 to 14 are views showing a relationship among a conductivity, a temperature, and a phase difference.

More specifically, the correction circuit 38 stores data showing the relationship between a conductivity difference and a phase difference correction value as shown in FIG. 12. In this case, the conductivity is obtained from a measured and stored conductivity of liquid whose density is zero and its corresponding conductivity signal. Then, if the correction circuit 38 receives the conductivity signal, the correction circuit 38 obtains a difference $\Delta\theta'$ between the phase difference $\Delta\theta$, which is from the phase detector 30, and the phase difference correction value $\Delta\theta\sigma$ from the relationship between the conductivity difference and the phase difference correction value $\Delta\theta\sigma$.

$$\Delta\theta' = \Delta\theta - \Delta\theta\sigma$$

The phase difference $\Delta\theta'$ is sent to the signal converter 31. The signal converter 31 obtains density of the measuring matter such as sludge from the relationship (working curve data) between the phase difference $\Delta\theta'$ and density shown in FIG. 14. Then, the signal converter 31 outputs a current signal in accordance with the obtained density, and the current signal is sent to a plant (not shown) through an output circuit 32.

Figure 13:
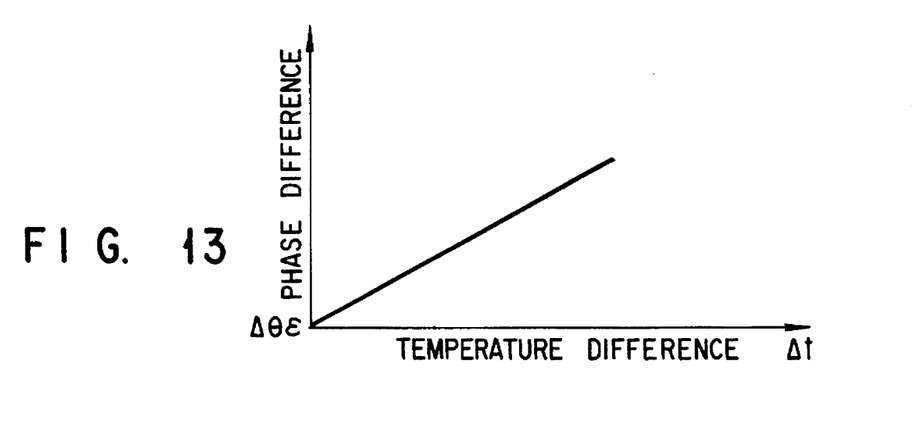
Figure 14:
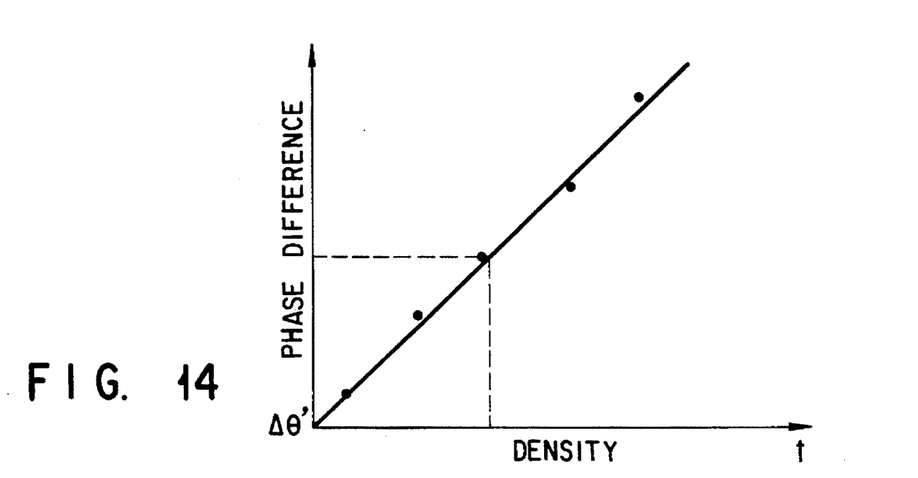

The following will explain the temperature correction with reference to FIG. 13.

More specifically, the correction circuit 38 stores data showing the relationship between a temperature difference, which is obtained from a measured and stored temperature of liquid whose density is zero and its corresponding temperature signal, and a phase difference correction value $\Delta\theta\epsilon$ as shown in FIG. 13. Then, if the correction circuit 38 receives the temperature signal, the correction circuit 38 obtains a difference $\Delta\theta'$ between the phase difference $\Delta\theta$, which is from the phase detector 30, and the phase difference correction value $\Delta\theta\epsilon$ from the relationship between the temperature difference and the phase difference correction value $\Delta\theta\epsilon$.

$$\Delta\theta' = \Delta\theta - \Delta\theta\epsilon$$

The phase difference $\Delta\theta'$ is sent to the signal converter 31. The signal converter 31 obtains density of the measuring matter such as sludge from the relationship (working curve data) between the phase difference $\Delta\theta'$ and density shown in FIG. 14. Then, the signal converter 31 outputs a current signal in accordance with the obtained density, and the current signal is sent to a plant (not shown) through an output circuit 32.

Moreover, in the case that both the conductivity correction and the temperature correction are performed, the signal converter 31 receives the conductivity signal and the temperature signal, the signal converter 31 obtains the phase difference correction values $\Delta\theta\sigma$ and $\Delta\theta\epsilon$, and a difference $\Delta\theta'$ between the phase difference $\Delta\theta$ and the phase difference correction values $\Delta\theta\sigma$ and $\Delta\theta\epsilon$.

$$\Delta\theta' = \Delta\theta - \Delta\theta\sigma - \Delta\theta\epsilon$$

The phase difference $\Delta\theta'$ is sent to the signal converter 31. The signal converter 31 obtains density of the matter to be measured such as sludge from the relationship (working curve data) between the phase difference $\Delta\theta'$ and temperature shown in FIG. 14. Then, the signal converter 31 outputs a current signal in accordance with the obtained density, and the current signal is sent to a plant (not shown) through an output circuit 32.

As mentioned above, in the second embodiment, the same technical advantage as the first embodiment can be obtained. Moreover, the following special technical advantage can be obtained.

That is, since the conductivity of the object of the density measurement is measured and the phase difference $\Delta\theta$ is corrected, the conductivity can be little influenced by an ion component which is dissolved in sludge.

Moreover, since the temperature of, e.g., sludge is measured and the phase difference $\Delta\theta$ is corrected, the conductivity can be little influenced by an ion component which is dissolved in sludge. Also, even if the relative dielectric constant is changed, such an influence can be controlled and the accurate density measurement can be performed.

As mentioned above, according to the present invention, since the density can be measured by use of the microwave of the frequency band of 1.4 to 1.75 -[GHz]-(the frequency bond of 1.55 to 1.60 -[GHz]-as a practice use, the density of the measuring object can be measured without having any adhesive onto the measuring matter and receiving the influence of the gas bubble in fluid. Moreover, according to the present invention, the density can be easily measured even in a state that the measuring object is completely dissolved in fluid. Furthermore, according to the present invention, the microwave of the frequency band of 1.55 to 1.60 -[GHz]-is used, thereby making it possible to largely improve the accuracy of the density measurement.

Additional advantages and modifications will readily occur to those skilled in the art. Therefore, the invention in its broader aspects is not limited to the specific details, and representative devices, shown and described herein. Accordingly, various modifications may be made without departing from the spirit or scope of the general inventive concept as defined by the appended claims and their equivalents.

What is claimed is:

1. A densitometer using a microwave, comprising:

a microwave detection section for producing a first microwave receiving signal by transmitting and receiving a microwave of a frequency band of 1.4 GHz to 1.75 GHz to and from a reference fluid, and a second microwave receiving signal by transmitting and receiving a microwave of a frequency band of 1.4 GHz to 1.75 GHz to and from a measuring fluid;

a phase detection section for obtaining a phase difference between said first microwave receiving signal and said second microwave receiving signal, said phase detection section comprising, phase lag detection means for detecting a first phase lag of the first microwave receiving signal and a second phase lag of the second microwave receiving signal, and phase difference detection means for obtaining a phase difference between the first and second microwave receiving signals based on the first and second phase lags detected by said phase lag detection means; and a density calculation section for calculating the density of the measuring fluid based on said phase difference obtained by said phase detection section.

2. A densitometer using a microwave according to claim 1, wherein said microwave detection section comprises:

a detection pipe member through which the measuring fluid flows;

a microwave transmission section, provided in said detection pipe member, for transmitting the microwave of the frequency band of 1.4 [GHz] to 1.75 547 GHz; and a microwave receiving section, provided in said detection pipe member to be opposite to said microwave transmission section, for receiving the microwave of the frequency band of 1.4 [GHz] to 1.75 [GHz].

3. A densitometer using a microwave according to claim 1, wherein said microwave detection section comprises:

a detection pipe member through which the measuring fluid flows and which includes first and second opening windows formed in facing opposition to each other;

a fist insulation member airtightly provided in said first opening window;

a microwave transmission antenna, airtightly provided in said first insulation member, for transmitting the microwave of the frequency band of 1.4 GHz to 1.75 GHz;

a second insulation member airtightly provided in said second opening window; and a microwave receiving antenna, airtightly provided in said second insulation member, for receiving the microwave of the frequency band of 1.4 GHz to 1.75 GHz.

4. A densitometer using a microwave according to claim 3, wherein the microwave transmission antenna and the microwave receiving antenna are filled with a dielectric.

5. A densitometer using a microwave according to claim 3, wherein the microwave transmission antenna and the microwave receiving antenna are filled with a dielectric, and at least one of said first and second insulation members is formed of the same material as said dielectric or a material whose dielectric constant and permeability are close to said dielectric.

6. The densitometer using a microwave according to claim 1, wherein said phase lag detection means detects said first phase lag prior to detecting said second phase lag.

7. The densitometer according to claim 6, wherein said phase detection section further comprises:

storing means for storing first phase by data corresponding to said first phase lag; and wherein said phase difference detection section obtains said phase difference based on the first phase lag stored in said storing means and the second phase lag obtained when the measuring fluid is flowed in the detection pipe member.

8. A densitometer using a microwave according to claim 1, further comprising a correction section for correcting said phase difference based on a difference between at least one of the first conductivity and first temperature of the reference fluid and at least one of the second conductivity and second temperature of the measuring fluid.

9. A densitometer using a microwave according to claim 1, further comprising a correction section for correcting said phase difference based on a difference between the first conductivity of the reference fluid and the second conductivity of the measuring fluid.

10. A densitometer using a microwave according to claim 1, further comprising a correction section for correcting said phase difference based on a difference between the first temperature of the reference fluid and the second temperature of the measuring fluid.

11. A densitometer using a microwave, comprising:

a microwave detection section for producing a first microwave receiving signal by transmitting and receiving a microwave of a frequency band of 1.4 GHz to 1.75 GHz to and from a reference fluid, and a second microwave receiving signal by transmitting and receiving a microwave of a frequency band of 1.4 GHz to 1.75 GHz to and from a measuring fluid;

a phase detection section for obtaining a phase difference between said first microwave receiving signal and said second microwave receiving signal, said phase detection section comprising, phase lag detection means for detecting a first phase lag of the first microwave receiving signal and a second phase lag of the second microwave receiving signal, and phase difference detection means for obtaining a phase difference between the first and second microwave receiving signals based on the first and second phase lags detected by said phase lag detection means;

a correction section for correcting said phase difference based on a difference between at least one of the first conductivity and first temperature of the reference fluid and at least one of the second conductivity and second temperature of the measuring fluid; and a density calculation section for calculating the density of the measuring fluid based on said corrected phase difference obtained by said correction section.

12. A densitometer using a microwave according to claim 11, wherein said microwave detection section comprises:

a detection pipe member through which the measuring fluid flows;

a microwave transmission section, provided in said detection pipe member, for transmitting the microwave of the frequency band of 1.4 GHz to 1.75 GHz; and a microwave receiving section, provided in said detection pipe member to be opposite to said microwave transmission section, for receiving the microwave of the frequency band of 1.4 GHz to 1.75 GHz.

13. A densitometer using a microwave according to claim 11, wherein said microwave detection section comprises:

a detection pipe member through which the fluid flows and which includes first and second opening windows formed in facing opposition to each other;

a first insulation member airtightly provided in said first opening window;

a microwave transmission antenna, airtightly provided in said first insulation member, for transmitting the microwave of the frequency band of 1.4 GHz to 1.75 GHz;

a second insulation member airtightly provided in said second opening window; and a microwave receiving antenna, airtightly provided in said second insulation member, for receiving the microwave of the frequency band of 1.4 GHz to 1.75 GHz.

14. A densitometer using a microwave according to claim 13, wherein the microwave transmission antenna and the microwave receiving antenna are filled with a dielectric.

15. A densitometer using a microwave according to claim 13, wherein the microwave transmission antenna and the microwave receiving antenna are filled with a dielectric, and at least one of said first and second insulation members is formed of the same material as said dielectric or a material whose dielectric constant and permeability are close to said dielectric.

16. The densitometer using a microwave according to claim 11, wherein said phase lag detection means detects said first phase lag prior to detecting said second phase lag.

17. The densitometer according to claim 16, wherein said phase detection section further comprises:

storing means for storing first phase lag data corresponding to said first phase lag; and wherein said phase difference detection section obtains said phase difference based on the first phase lag stored in said storing means and the second phase lag obtained when the measuring fluid is flowed in the detection pipe member.

18. A densitometer using a microwave according to claim 11, wherein said correction section comprises means for correcting said phase difference based on a difference between the first conductivity of the reference fluid and the second conductivity of the measuring fluid.

19. A densitometer using a microwave according to claim 11, wherein said correction section for correcting said phase difference based on a difference between the first temperature of the reference fluid and the second temperature of the measuring fluid.

* * * * *